(12) United States Patent
Sasaki et al.

(10) Patent No.: US 9,691,433 B2
(45) Date of Patent: Jun. 27, 2017

(54) MEDICAL IMAGE DIAGNOSIS APPARATUS AND MEDICAL IMAGE PROCCESSING APPARATUS

(71) Applicant: Toshiba Medical Systems Corporation, Otawara-shi (JP)

(72) Inventors: Takuya Sasaki, Nasu (JP); Kuramitsu Nishihara, Otawara (JP); Mio Azegami, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/689,429

(22) Filed: Apr. 17, 2015

(65) Prior Publication Data

US 2015/0302605 A1    Oct. 22, 2015

(30) Foreign Application Priority Data

Apr. 18, 2014    (JP) .................... 2014-086673

(51) Int. Cl.
| | |
|---|---|
| *G06K 9/00* | (2006.01) |
| *G11B 27/10* | (2006.01) |
| *A61B 8/14* | (2006.01) |
| *A61B 6/03* | (2006.01) |
| *A61B 5/055* | (2006.01) |

(Continued)

(52) U.S. Cl.
CPC .......... *G11B 27/102* (2013.01); *A61B 5/0456* (2013.01); *A61B 5/055* (2013.01); *A61B 5/7289* (2013.01); *A61B 6/032* (2013.01); *A61B 6/463* (2013.01); *A61B 6/467* (2013.01); *A61B 6/486* (2013.01); *A61B 8/14* (2013.01); *A61B 8/463* (2013.01); *A61B 8/467* (2013.01); *G11B 27/005* (2013.01); *G11B 27/34* (2013.01); *G09G 2310/027* (2013.01); *G09G 2310/0291* (2013.01); *G09G 2310/08* (2013.01)

(58) Field of Classification Search
CPC ....... A61B 8/463; A61B 5/0456; A61B 5/055; A61B 5/7289; A61B 6/463; A61B 6/467; A61B 6/486; A61B 8/14; A61B 8/467; A61B 6/032
See application file for complete search history.

(56) References Cited

U.S. PATENT DOCUMENTS 6,181,870 B1 * 1/2001 Okada .................. G11B 7/0037
386/241
8,538,100 B2 * 9/2013 Mine .................... A61B 6/5247
382/128

(Continued)

FOREIGN PATENT DOCUMENTS

JP    64-018189 A    1/1989

*Primary Examiner* — Jonathan S Lee
(74) *Attorney, Agent, or Firm* — Oblon, McClelland, Maier & Neustadt, L.L.P.

(57) ABSTRACT

A medical image diagnosis apparatus including an image collection system that collects first dynamic images extending over a first period and a display control circuit that uses the first dynamic images and time information related to an image corresponding to a first predetermined time phase in the first period to simultaneously display the first dynamic images, the first predetermined time phase, and a relationship of the image currently displayed with a time phase in the first period at least in a predetermined period going back from the predetermined time phase in a monitor.

8 Claims, 14 Drawing Sheets

(51) Int. Cl.
*A61B 8/00* (2006.01)
*A61B 6/00* (2006.01)
*A61B 5/0456* (2006.01)
*A61B 5/00* (2006.01)
*G11B 27/00* (2006.01)
*G11B 27/34* (2006.01)

(56) References Cited

U.S. PATENT DOCUMENTS

| | | | |
|---|---|---|---|
| 8,861,809 B2* | 10/2014 | Matsue | G06F 19/321 |
| | | | 382/128 |
| 9,345,454 B2* | 5/2016 | Brandl | A61B 8/0883 |
| 2004/0066389 A1* | 4/2004 | Skyba | A61B 8/08 |
| | | | 345/619 |
| 2009/0148020 A1* | 6/2009 | Sugiura | A61B 5/055 |
| | | | 382/131 |
| 2009/0149749 A1* | 6/2009 | Heron | A61B 8/08 |
| | | | 600/437 |
| 2010/0067767 A1* | 3/2010 | Arakita | A61B 6/507 |
| | | | 382/131 |
| 2010/0234731 A1* | 9/2010 | Lu | A61B 8/06 |
| | | | 600/454 |
| 2011/0144494 A1* | 6/2011 | Mehi | B06B 1/0622 |
| | | | 600/441 |
| 2014/0128738 A1* | 5/2014 | White | A61B 8/543 |
| | | | 600/447 |

* cited by examiner

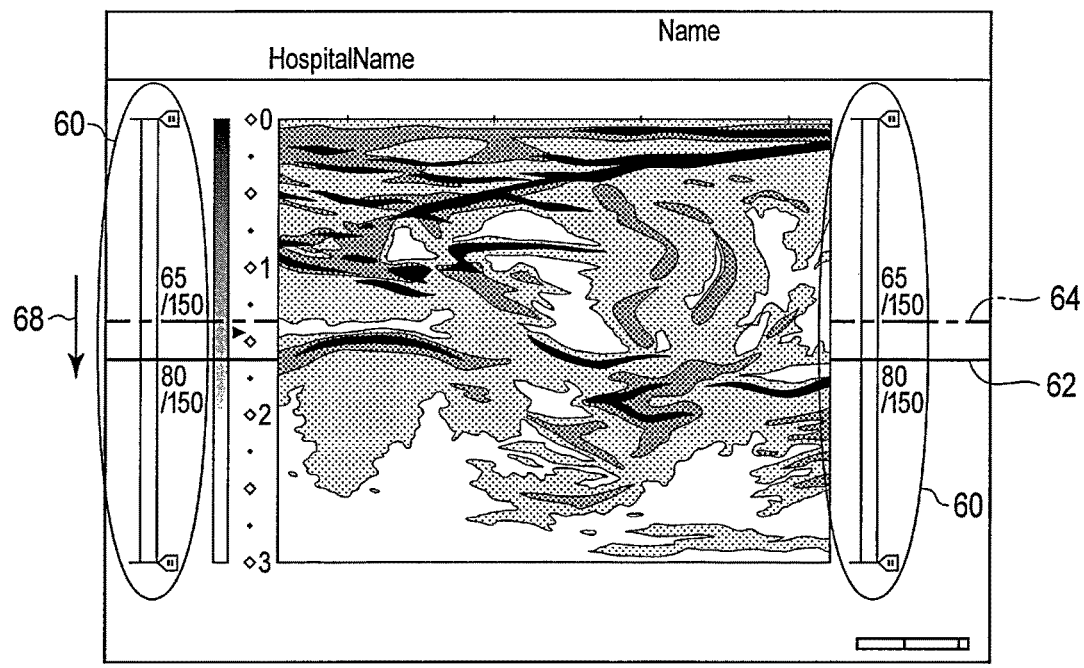
F I G. 7A
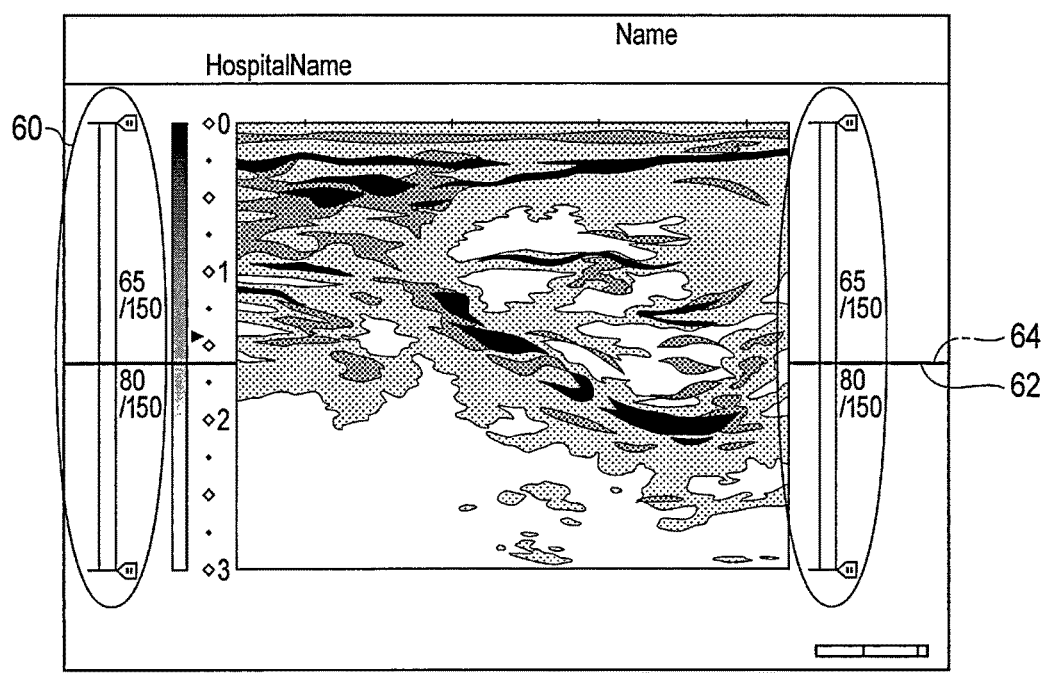
F I G. 7B

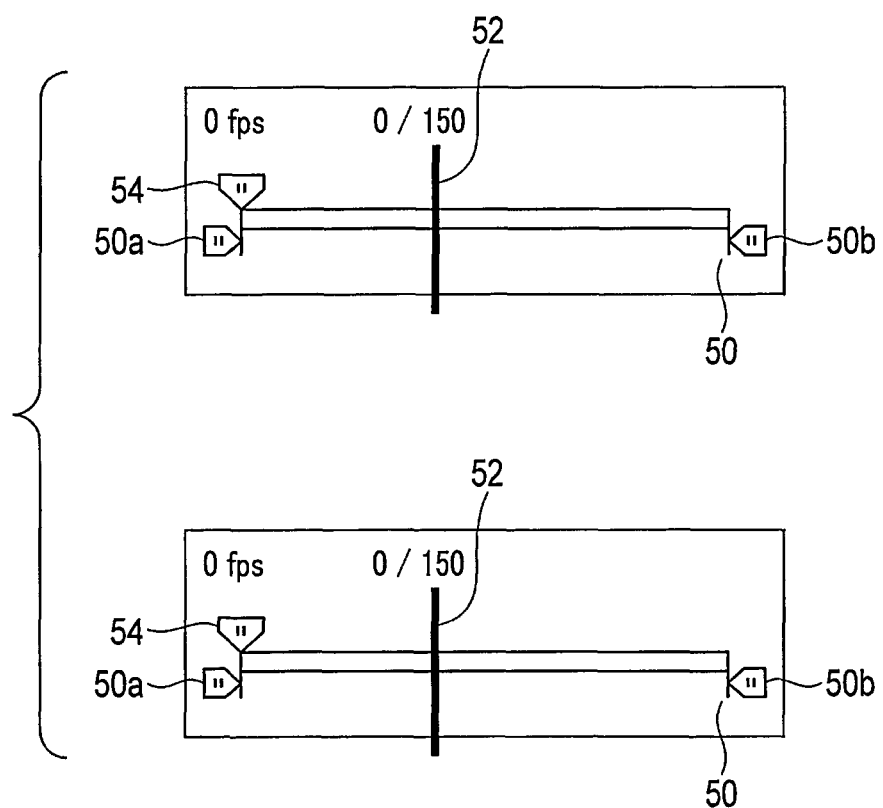
F I G. 10

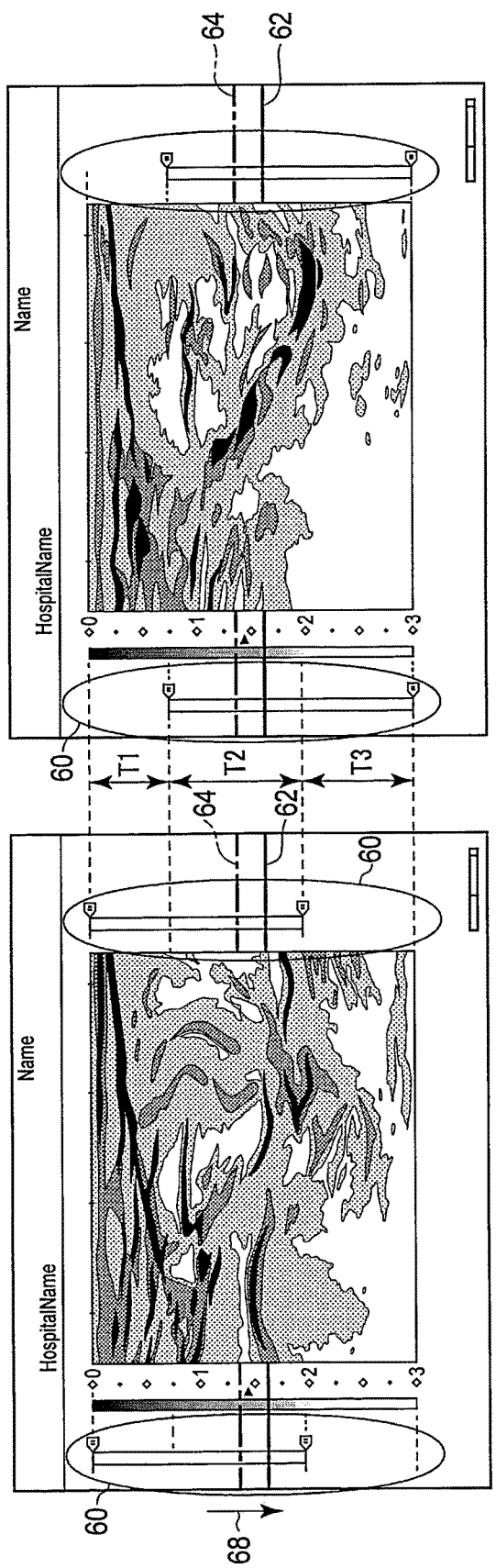
F I G. 12

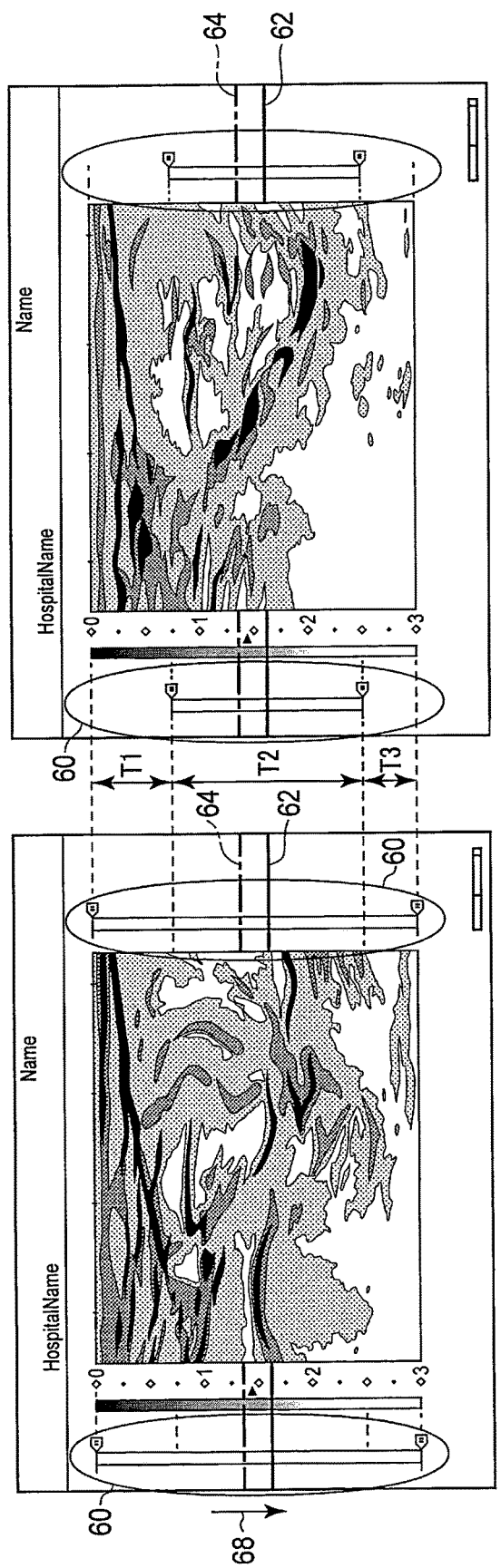
F I G. 13

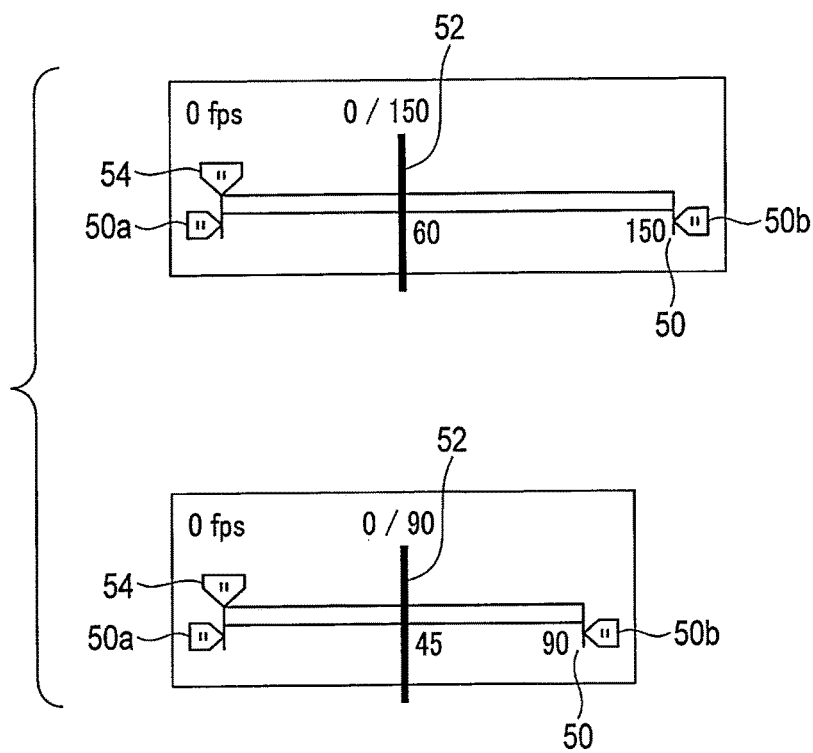
F I G. 14
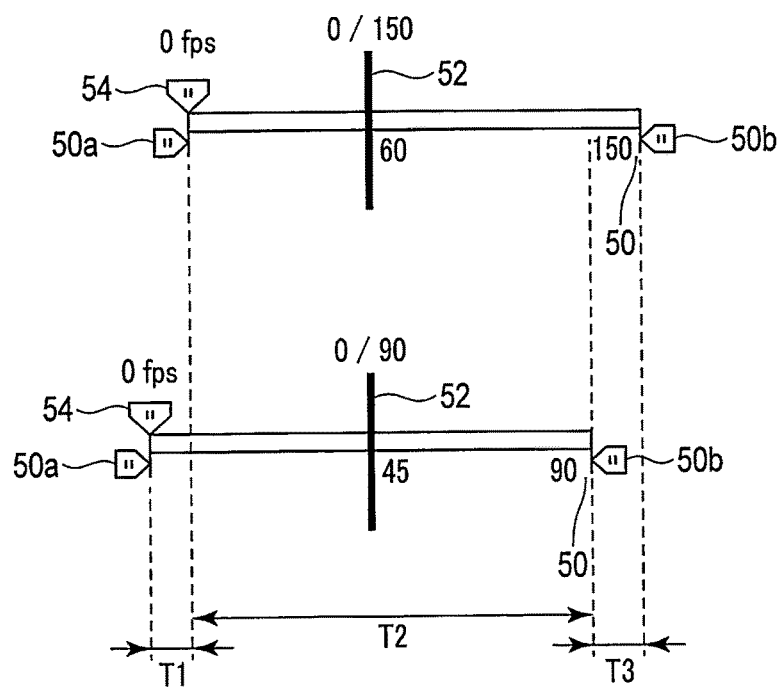
F I G. 15

MEDICAL IMAGE DIAGNOSIS APPARATUS AND MEDICAL IMAGE PROCCESSING APPARATUS

CROSS-REFERENCE TO RELATED APPLICATIONS

This application is based upon and claims the benefit of priority from the prior Japanese Patent Application No. 2014-086673, Apr. 18, 2014, the entire contents of which are incorporated herein by reference.

FIELD

Embodiments described herein relate generally to a medical image diagnosis apparatus and a medical image processing apparatus.

BACKGROUND

Medical image diagnosis apparatuses image the inside of a subject by various techniques and include various modalities such as an X-ray CT apparatus, a magnetic resonance imaging apparatus, an X-ray diagnosis apparatus, and an ultrasonic diagnosis apparatus. For example, the ultrasonic diagnosis apparatus collects organism information by emitting an ultrasonic pulse generated by a vibration element provided in an ultrasonic probe and into the subject and receiving an ultrasonic reflected wave generated by differences of acoustic impedances of the subject organism by the vibration element. The real-time display of dynamic images can be realized only by bringing the ultrasonic probe into contact of the surface of a body.

Ultrasonic images acquired by the ultrasonic diagnosis apparatus can be stored as still images or dynamic images. If a user is interested in images in a specific time phase of dynamic images, the user can also store information identifying the specific time phase as a "marker" together with the images. The stored still images or dynamic images can be played back retrospectively by the ultrasonic diagnosis apparatus, an ultrasonic image processing apparatus (medical workstation) or the like.

In a conventional storage method and playback method of medical images including ultrasonic images, the following problems are posed.

When, for example, ultrasonic images are stored as dynamic images extending over a fixed period, images of interest to actual imaging diagnosis are images corresponding to a predetermined time phase (frame). In a conventional ultrasonic diagnosis apparatus, however, the whole dynamic image storage range is intended for inspection. Thus, when dynamic images are retrospectively played back, a problem that it is difficult to identify a time phase of interest is posed. In recent years, apparatuses that automatically insert a marker in a change point of the inspection item such as a mode transition or manually insert a marker in a focused time phase (frame) during inspection have been proposed. However, the dynamic image storage range remains to be wide and the fact that a lot of time and effort are needed to reach a desired image remains unchanged. Further, apparatuses capable of individually designating the dynamic image storage range based on the time or the heart rate have been proposed. However, an image of the specific time phase operated to be frozen is not necessarily included in the set dynamic image storage range. Thus, to store an image of the specific time phase operated to be frozen by always including the image in dynamic images, an operation to designate the storage range individually and explicitly is separately needed. Therefore, it is still troublesome for the operator and adequate ease of use is not yet realized.

Embodiments described herein are developed in view of the above circumstances and an object thereof is to provide a medical image diagnosis apparatus and a medical image processing apparatus capable of always storing images of temporal interest and grasping images of temporal interest easily and intuitively in retrospective playback.

BRIEF DESCRIPTION OF THE DRAWING

FIGS. 7A and 7B are diagrams showing another example (another example of the slide bar) of the image of interest explicit information generated or displayed in playback processing of dynamic image data according to the present embodiment;

FIG. 10 is a diagram illustrating the synchronous playback mode example 1;

FIG. 12 is a diagram illustrating a synchronous playback mode example 3;

FIG. 13 is a diagram illustrating the synchronous playback mode example 3;

FIG. 14 is a diagram illustrating a synchronous playback mode example 4;

FIG. 15 is a diagram illustrating the synchronous playback mode example 4; and

DETAILED DESCRIPTION

Figure 1:
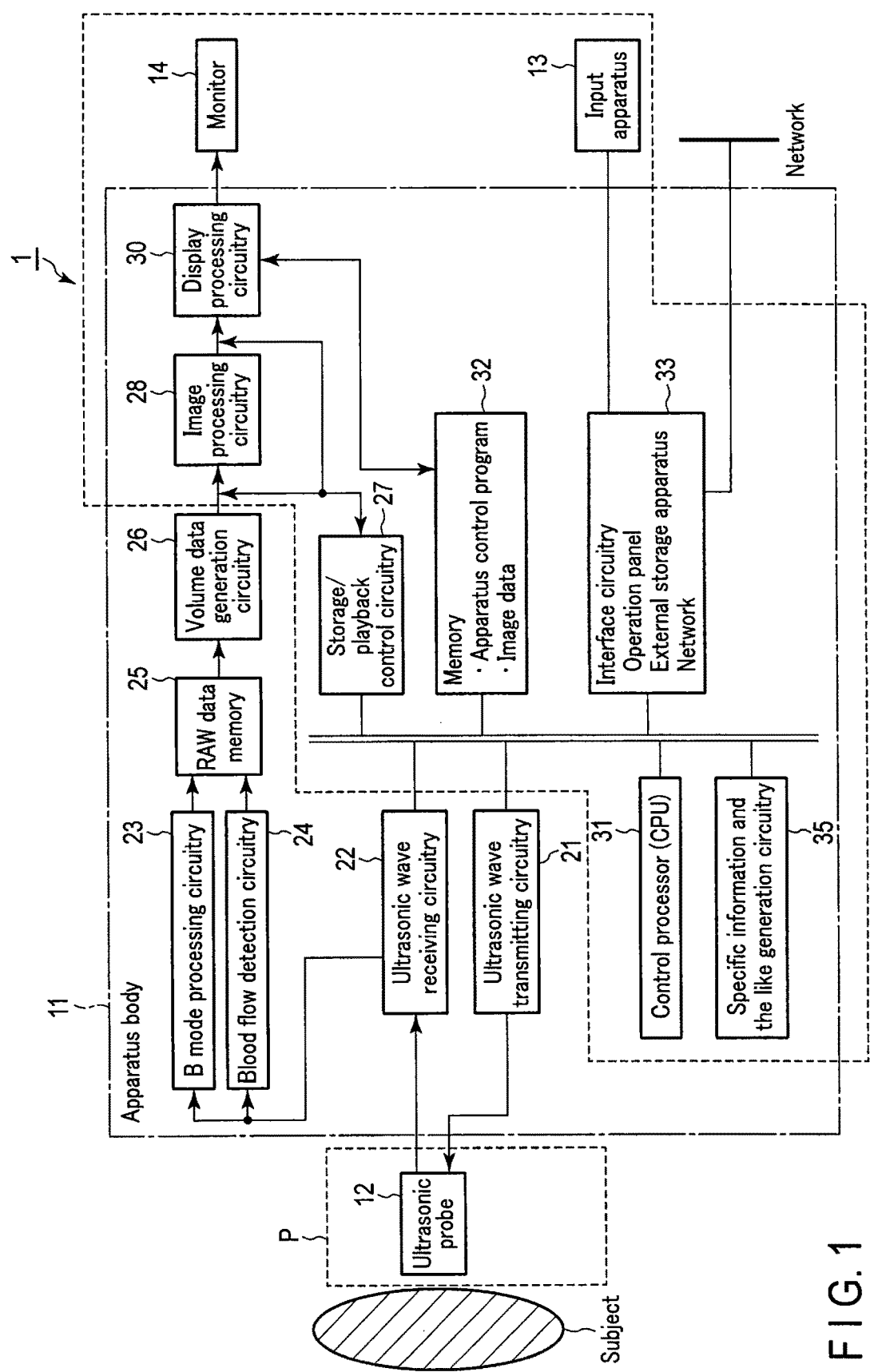
FIG. 1 shows a block diagram of an ultrasonic diagnosis apparatus 1 according to an embodiment.

A medical image diagnosis apparatus disclosed by this embodiment including an image collection system that collects first dynamic images extending over a first period and a display control circuit that uses the first dynamic images and time information related to an image corresponding to a first predetermined time phase in the first period to simultaneously display the first dynamic images, the first predetermined time phase, and a relationship of the image currently displayed with a time phase in the first period at least in a predetermined period going back from the predetermined time phase in a monitor.

Hereinafter, an ultrasonic diagnosis apparatus according to the present embodiment will be described with reference to the drawings. In the description that follows, the same reference numerals are attached to structural elements having substantially the same function and configuration and a duplicate description will be provided only when necessary.

FIG. 1 shows a block diagram of the ultrasonic diagnosis apparatus 1 according to the present embodiment. The ultrasonic diagnosis apparatus 1 shown in FIG. 1 includes an ultrasonic probe 12, an input apparatus 13, a monitor 14, an ultrasonic wave transmitting circuit 21, an ultrasonic wave receiving circuit 22, a B mode processing circuit 23, a blood flow detection circuit 24, a RAW data memory 25, a volume data generation unit 26, a storage/playback control unit 27, an image processing unit 28, a display processing unit 30, a control processor (CPU) 31, a storage unit 32, an interface unit 33, and a specific information and the like generation unit 35.

The ultrasonic probe 12 is a device (probe) that transmits an ultrasonic wave to a subject, typically an organism, and receives a reflected wave from the subject based on the transmitted ultrasonic wave and has a plurality of piezoelectric vibrators (ultrasonic transducers), matching layers, and backing materials arranged at the tip thereof. The piezoelectric vibrator transmits an ultrasonic wave in a desired direction within a scan region based on a drive signal from the ultrasonic wave transmitting circuit 21 and converts a reflected wave from the subject into an electric signal. The matching layer is an intermediate layer provided in the piezoelectric vibrator to efficiently propagate ultrasonic wave energy. The backing material prevents propagation of the ultrasonic wave in a rear direction from the piezoelectric vibrator. When an ultrasonic wave is transmitted from the ultrasonic probe 12 to the subject, the transmitted ultrasonic wave is successively reflected by the surface of discontinuity of acoustic impedance of intracorporeal tissues and received by the ultrasonic probe 12 as an echo signal. The amplitude of the echo signal depends on a difference of acoustic impedances of surfaces of discontinuity where the ultrasonic wave is reflected. The echo when a transmitted ultrasonic pulse is reflected by a moving blood flow undergoes a frequency deviation depending on the speed component of the moving body in an ultrasonic wave transmitting/receiving direction due to the Doppler effect. In the present embodiment, it is assumed that the ultrasonic probe 12 is a one-dimensional array probe in which a plurality of ultrasonic vibrators is arranged along a predetermined direction. However, the ultrasonic probe 12 is not limited to such an example and may be a two-dimensional array probe (probe in which a plurality of ultrasonic vibrators is arranged like a two-dimensional matrix) or a mechanical 4D probe (probe capable of performing an ultrasonic scan while mechanically agitating a row of ultrasonic vibrators in a direction perpendicular to the arrangement direction thereof) capable of acquiring volume data.

The input apparatus 13 is connected to an apparatus body 11 and includes various switches, buttons, a trackball, a mouse, a keyboard or the like to incorporate various instructions, conditions, setting instructions of the region of interest (ROI), various image quality condition setting instructions and the like from the operator into the apparatus body 11.

The monitor 14 displays morphological information inside an organism or blood flow information as images based on a video signal from the display processing unit 30.

The monitor 14 also displays ultrasonic images played back by a dynamic image data playback control function described later in a predetermined form together with predetermined information.

The ultrasonic wave transmitting circuit 21 includes a trigger generation circuit, a delay circuit, and a pulser circuit (not shown). In the trigger generation circuit, a trigger pulse to form a transmitted ultrasonic wave is repeatedly generated at a predetermined rate frequency fr Hz (period; 1/fr s). In the delay circuit, a delay time necessary to converge an ultrasonic wave like a beam for each channel and also to determine transmission directivity is given to each trigger pulse. In the pulser circuit, a drive pulse is applied to the probe 12 in the timing based on the trigger pulse.

The ultrasonic wave receiving circuit 22 includes an amplifier circuit, an A/D converter, a delay circuit, and an adder. In the amplifier circuit, an echo signal incorporated via the probe 12 amplifies for each channel. In the A/D converter, an amplified analog echo signal is converted into a digital echo signal. In the delay circuit, reception directivity is determined for the digitally converted echo signal and a delay time necessary to perform a receiving dynamic focus is given and then, addition processing is performed by the adder. By this addition, reflection components from the direction in accordance with the reception directivity of the echo signal are emphasized and a comprehensive beam of ultrasonic wave transmission and reception is formed by the reception directivity and the transmission directivity.

The B mode processing circuit 23 receives an echo signal from the receiving unit 22 and performs logarithmic amplification, envelope detection processing and the like thereon to generate data in which signal strength is represented by brightness in luminance.

The blood flow detection circuit 24 extracts a blood flow signal from an echo signal received from the receiving unit 22 to generate blood flow data. Extraction of the blood flow is normally carried out by CFM (Color Flow Mapping). In this case, the blood flow signal is analyzed to determine blood flow information such as the average speed, dispersion, and power as blood flow data in multiple points.

The RAW data memory 25 uses a plurality of pieces of B mode data received from the B mode processing circuit 23 to generate B mode RAW data as B mode data on a three-dimensional ultrasonic scanning line. The RAW data memory 25 also uses a plurality of pieces of blood flow data received from the blood flow detection circuit 24 to generate blood flow RAW data as blood flow data on a three-dimensional ultrasonic scanning line. A three-dimensional filter may be inserted after the RAW data memory 25 for spatial smoothing for the purpose of reducing noise or making image connection better.

The volume data generation unit 26 is realized by, for example, a memory and a predetermined processor and generates B mode volume data and blood flow volume data by making a RAW-voxel conversion including interpolation processing to which spatial position information is added.

The storage/playback control unit 27 is realized by, for example, a memory and a predetermined processor and determines the dynamic image storage range relative to a frame of temporal interest (hereinafter, a frame of temporal interest will be called a "frame of interest" and an image corresponding to the frame of interest will be called an "image of interest"). Also in the retrospective playback of ultrasonic images, the storage/playback control unit 27 controls the dynamic image playback such that the frame of interest (and a region of interest in the relevant frame) is explicitly shown to the observer. The dynamic image data storage control function and the dynamic image data playback control function realized by the storage/playback control unit 27 will be described in detail later.

The image processing unit 28 is realized by, for example, a memory and a predetermined processor and performs predetermined image processing such as volume rendering, multi planar reconstruction (MPR), and maximum intensity projection (MIP) on volume data received from the volume data generation unit 26. Incidentally, a two-dimensional filter may be inserted after the image processing unit 28 for spatial smoothing for the purpose of reducing noise or making image connection better.

The display processing unit 30 performs various kinds of processing of the dynamic range, luminance (brightness), contrast, y curve correction, RGB conversion and the like on various kinds of image data generated or processed by the image processing unit 28.

The control processor 31 is realized by, for example, a memory and a predetermined processor, has a function as an information processing apparatus (computer), and controls the operation of each structural element. The control processor 31 also performs processing following the dynamic image data storage control function and the dynamic image data playback control function described later.

The storage unit 32 is configured by a magnetic disk, a magneto-optical disk, a semiconductor memory or the like and has a program to realize the dynamic image data storage/playback control function described later, a diagnostic protocol, transmission and reception conditions, and other data stored therein. In addition, the storage unit 32 is used to store images in an image memory (not shown) when necessary. Data in the storage unit 32 can be transferred to an external peripheral apparatus via the interface unit 33.

The interface unit 33 is an interface for the input apparatus 13, a network, and a new storage apparatus (not shown). Another apparatus can also be connected to the ultrasonic diagnosis apparatus body 11 via the interface unit 33. Data such as ultrasonic images obtained by the apparatus and analysis results can be transferred to another apparatus by the interface unit 33 via a network.

The specific information and the like generation unit 35 generates information to identify a predetermined time phase (or an image corresponding to the predetermined time phase) in a storage period and information to explicitly show the predetermined time phase (or the image corresponding to the predetermined time phase) in the storage period when each piece of processing following the dynamic image data storage control function and the dynamic image data playback control function is performed.

Next, the dynamic image data storage control function and the dynamic image data playback control function held by the ultrasonic diagnosis apparatus 1 will be described. The dynamic image data storage control function and the dynamic image data playback control function is used when, for example, live images of an ultrasonic diagnosis apparatus are captured/displayed and stored or dynamic image data acquired and stored and extending over a predetermined period is stored/played back again. In the present embodiment, a case when dynamic image data acquired by the ultrasonic diagnosis apparatus is stored and played back is taken as an example. However, the present embodiment is not limited to such an example and the functions are applicable when, for example, dynamic image data acquired by a different modality (medical image diagnosis apparatus) such as an X-ray computerized tomographic apparatus, a magnetic resonance imaging apparatus, and an X-ray diagnosis apparatus is stored or played back. When the dynamic image data storage control function or the dynamic image data playback control function is realized in a medical image processing apparatus, the medical image processing apparatus includes, for example, the configuration inside a broken line in FIG. 1.

(Dynamic Image Data Storage Control Function)

When dynamic image data extending over a predetermined period is stored, this function determines the storage range using the image of interest (frame of interest) as a reference and, instead of storing all dynamic image data, stores dynamic image data corresponding to the determined storage range as clips together with information to identify the image of interest.

Figure 2:
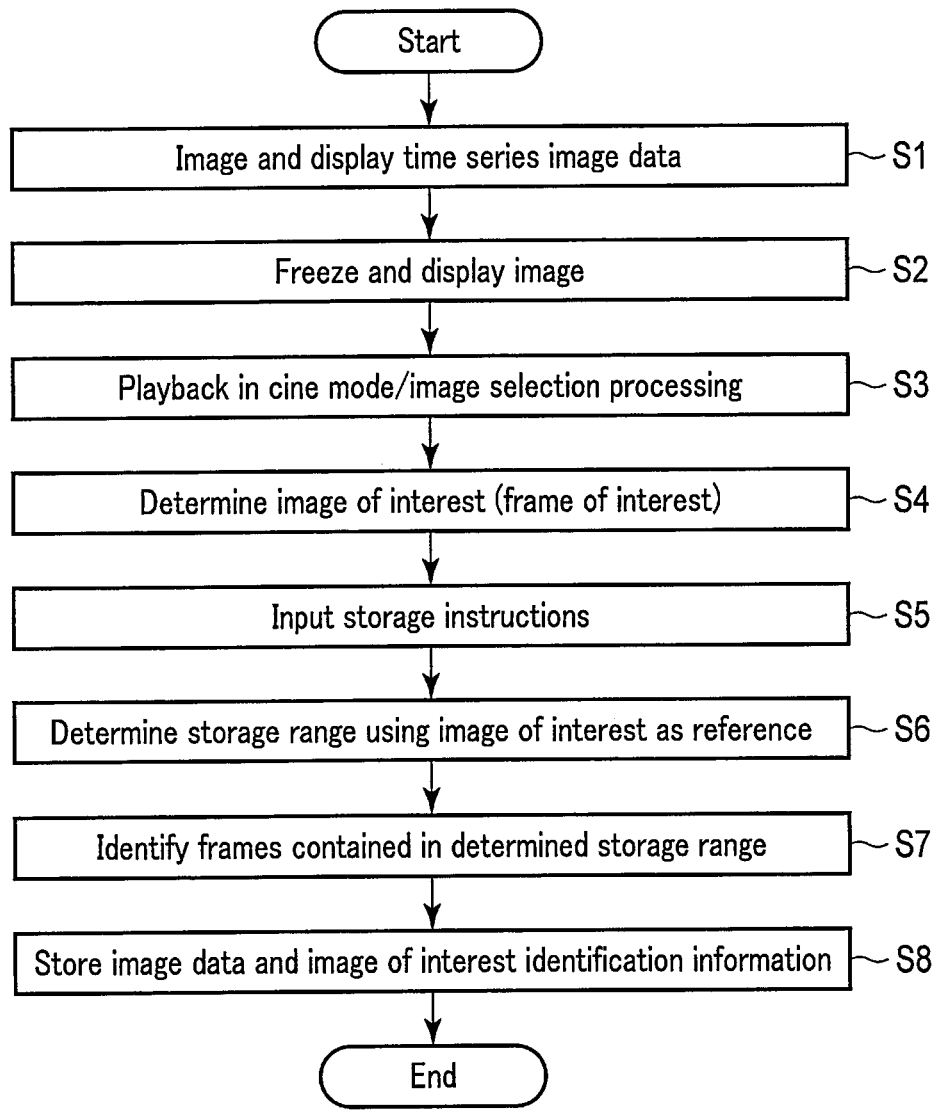
FIG. 2 is a flow chart showing the flow of storage processing of dynamic image data according to the present embodiment.

FIG. 2 is a flow chart showing the flow of each piece of processing performed in processing (image data storage control processing) following the image data storage control function. Hereinafter, content of the processing in each step will be described. To make the description more concrete, a case when image diagnosis of a central nerve running state of an arm is carried out in the plastic surgery field is assumed. In such a case, the ultrasonic probe 12 is arranged in a region of the arm to be diagnosed and a cross section image in each moving position is captured while moving the probe along the longitudinal direction. The observer grasps the running state of central nerves while observing the image in each moving position displayed as a dynamic image in real time with the movement of the ultrasonic probe 12.

In response to predetermined operation instructions, the control processor 31 performs imaging processing of a diagnosis object (in this case, the arm) to acquire time series image data (dynamic image data) and displays the data in the monitor 14 in a predetermined form as live images (step S1). The operator freezes and displays images in predetermined timing while observing ultrasonic images displayed as live images (step S2) and then performs image selection processing to select a desired image while playing back images in cine mode (step S3) to determine the image of interest (step S4). When image diagnosis of a central nerve running state of an arm is carried out, for example, an image including a portion in which the central nerve running state of the arm is visually recognized as discontinuous in dynamic images, an image corresponding to the time phase when the sight of the central nerve running state is lost, or an image corresponding to the time phase when a disease is visualized is determined as an image of interest.

Then, when a storage instruction is input by the operator (step S5), the storage/playback control unit 27 determines the storage range using the time phase corresponding to the image of interest as a reference (step S6). The storage range is determined based on a pre-selection from a plurality of preset storage conditions or initially set conditions.

Figure 3:
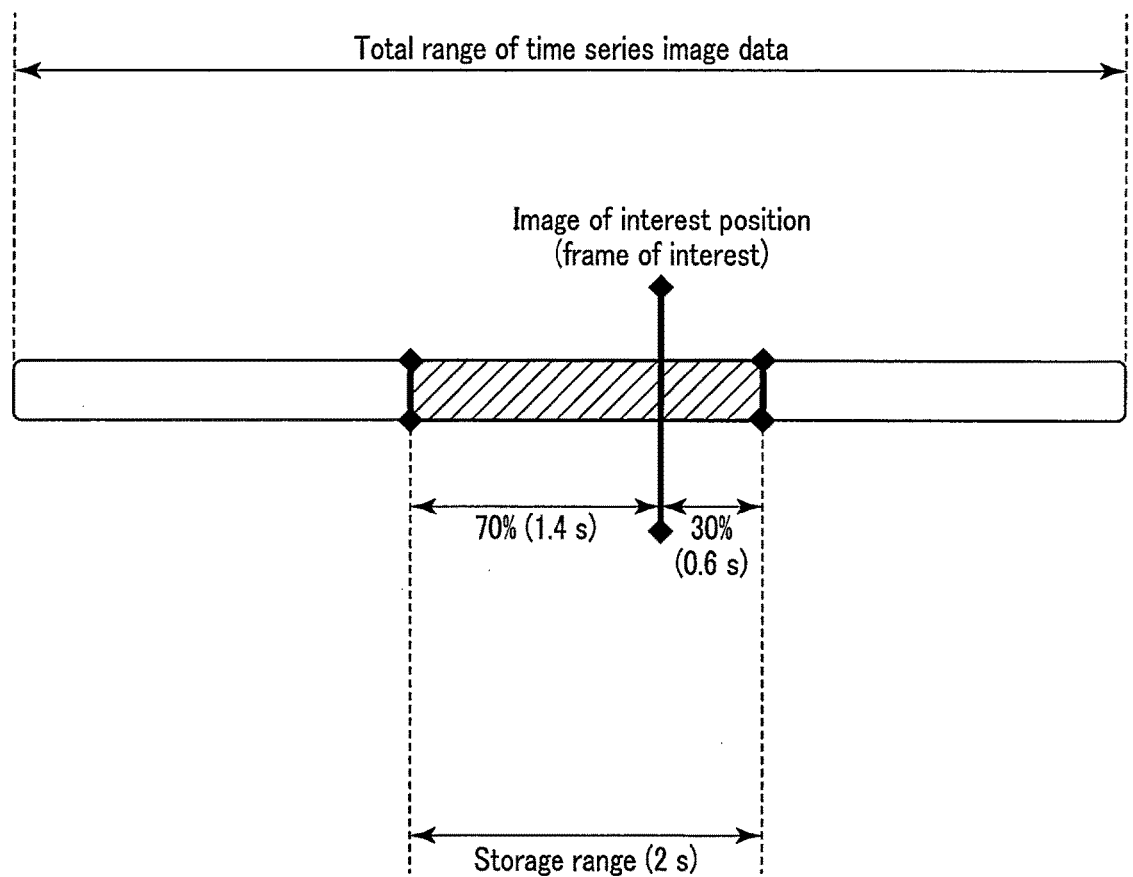
FIG. 3 is a diagram illustrating a storage range of storage processing of dynamic image data according to the present embodiment.

FIG. 3 is a diagram showing an example of preset storage conditions. If, for example, as shown in FIG. 3, the storage range is defined as a range corresponding to 2-second dynamic image data, the time phase corresponding to the image of interest is used as a reference and storage conditions are set as 1.4, which is 70% of the storage range before the time phase corresponding to the image of interest, and 0.6 s, which is 30% of the storage range after the time phase corresponding to the image of interest. The storage range after the time phase corresponding to the image of interest is made narrower as shown above because the importance of images acquired the image of interest (frame of interest) is generally considered to be low. The storage range after the time phase corresponding to the image of interest is set to 0.6 s corresponding to 30%, but if, for example, only 0.3 s of images after the time phase corresponding to the image of interest actually remain (that is, image data to be stored is less than the storage range), all image data included in the storage range is to be automatically stored.

If the storage range is determined, the storage/playback control unit 27 identifies image data (frames) included in the determined storage range from the time series image data (step S7) and stores image data included in the storage range, still image data of the image of interest, and image of interest identification information (for example, the position of the frame of interest in the storage range or the playback period, that is, information indicating No. of the image of interest (frame of interest) in the stored image data (frames)) to identify the image of interest in the storage range in the storage unit 32 as supplementary information of image data to be stored or by associating with image data to be stored. In addition to the image data included in the storage range, the storage/playback control unit 27 stores supplementary information such as annotations by associating with images (step S8). Further, the storage/playback control unit 27 stores the total number of frames of image data to be stored, the playback speed or playback time, and a core time phase of each frame when images are acquired by ECG synchronization in the storage unit 32 as supplementary information of image data to be stored or by associating with image data to be stored.

In step S4 described above, the operator observes images played back in cine mode and determines the image of interest to be the reference of the storage range by a manual operation from the input apparatus 13. However, the present embodiment is not limited to such an example and if the diagnosis object is, for example, a circulatory organ such as a heart, an image corresponding to a time phase identified by using an ECG waveform (for example, a telediastolic time phase, a telesystolic time phase and the like) may automatically be determined as an image of interest. Also, the length of the storage range can be determined like, for example, one heart beat period using the ECG waveform.

Figure 4:
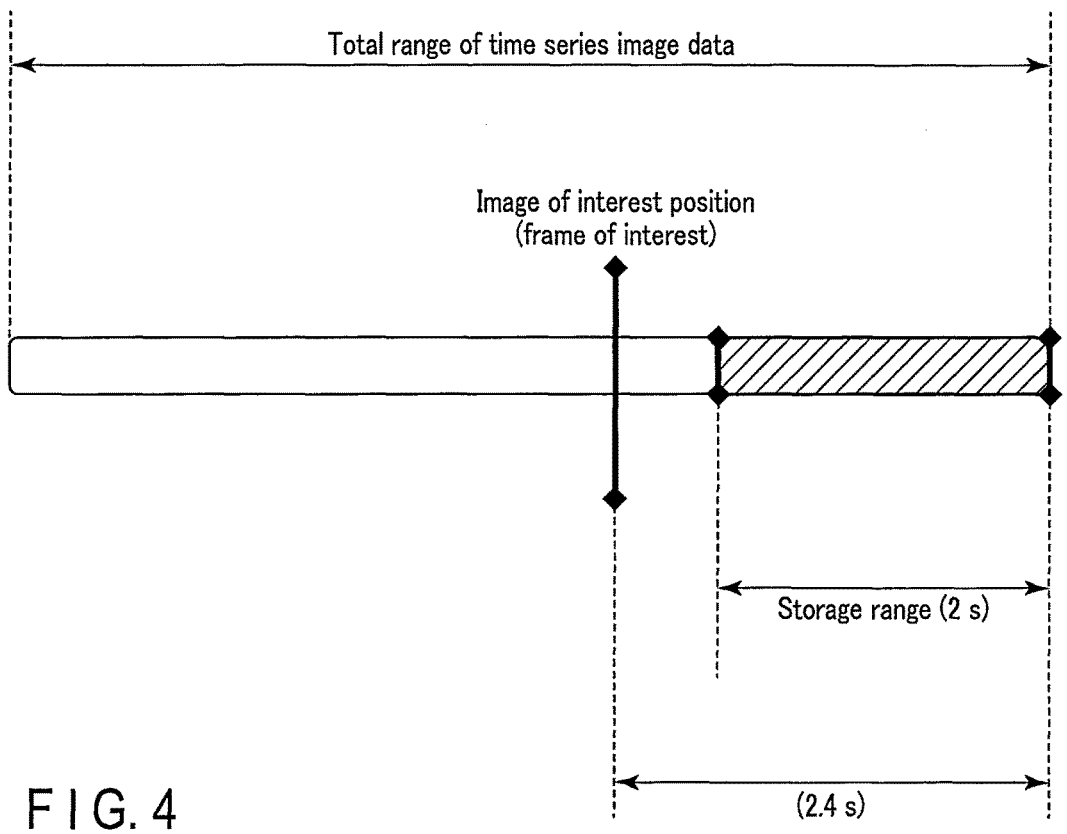
FIG. 4 is a diagram illustrating the storage range of storage processing of dynamic image data according to a conventional ultrasonic diagnosis apparatus.

FIG. 4 is a diagram illustrating dynamic image storage in a conventional ultrasonic diagnosis apparatus. When, for example, as shown in FIG. 4, the storage range is preset as "going back two seconds in time series image data from the last frame", if the image of interest is located in a position going back 2.4 seconds from the last frame, the image of interest is not included in the storage range and is not stored as dynamic image data.

According to the present ultrasonic diagnosis apparatus, by contrast, the storage range can be set such that an image of interest, which is used as a reference, corresponding to the time phase of temporal interest of dynamic image data extending over a predetermined period is always included therein. Thus, a situation in which the image of interest is not included in the stored dynamic image data can reliably be avoided.

In addition, using the image of interest as a reference, dynamic images can be stored by limiting to the range in which images are valuable for image diagnosis. Therefore, when dynamic images are retrospectively played back, the image of interest can be reached efficiently. Further, a storage area of the apparatus can be used efficiently with minimum waste.

(Dynamic Image Data Playback Control Function)

When dynamic image data extending over a predetermined period is played back, this function generates time information explicitly showing the time phase of the image of interest (frame of interest) in the predetermined period and using this information, displays the relationship between the time phase of the frame of interest in the predetermined period and the time phase in the predetermined period of the image currently displayed or time information indicating No. of the image of interest (frame of interest) in the image data of a plurality of frames corresponding to the predetermined period to be played back together with dynamic images. Accordingly, the observer can be notified of an imminent appearance of the frame of interest (that the frame of interest will be displayed in a few seconds) and the like, thereby drawing observer's attention so that observation timing of the frame of interest is not missed.

Figure 5:
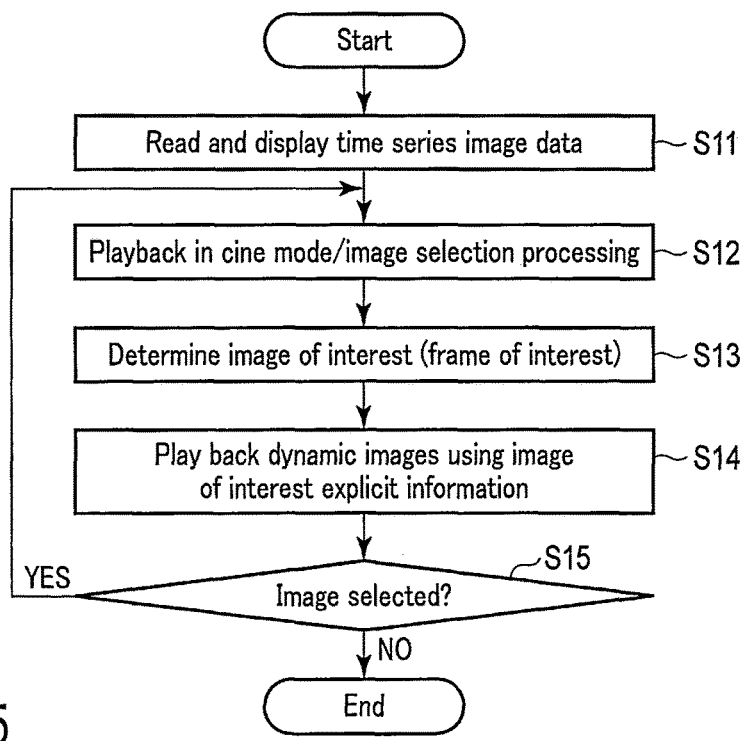
FIG. 5 is a flow chart showing the flow of playback processing of dynamic image data according to the present embodiment.

FIG. 5 is a flow chart showing the flow of each piece of processing performed in processing (image data playback control processing) following the dynamic image data playback control function. Hereinafter, content of the processing in each step will be described. To make the description more concrete, like in the image data storage control processing, a case when image diagnosis of a central nerve running state of an arm is carried out in the plastic surgery field is assumed.

In response to predetermined operation instructions, the control processor 31 reads time series image data of a diagnosis object (arm) from the storage unit 32 and displays the data in the monitor 14 in a predetermined form (step S11). The operator performs image selection processing to select a desired image while playing back the read time series image data in cine mode (step S12) to determine the image of interest (step S13).

When the image of interest is determined, the storage/playback control unit 27 plays back dynamic images using image of interest explicit information (step S14). Various forms can be used for playback of dynamic images using the image of interest explicit information. Hereinafter, each example will be described.

Example 1

Figure 6A:
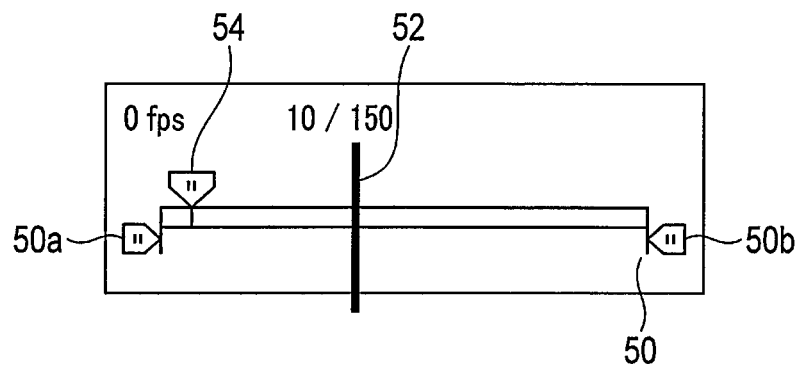
FIGS. 6A, 6B, and 6C are diagrams showing an example (slide bar) of image of interest explicit information generated or displayed in playback processing of dynamic image data according to the present embodiment.
Figure 6B:
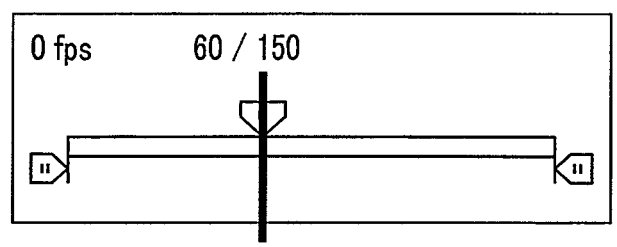
Figure 6C:
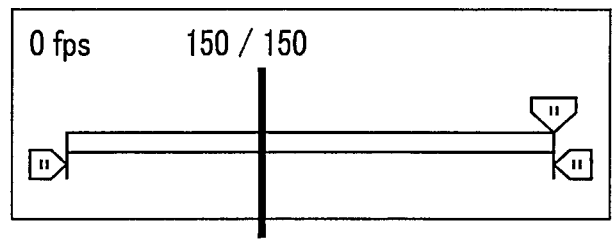

FIGS. 6A, 6B, and 6C are diagrams illustrating the playback of dynamic images using image of interest explicit information according to Example 1. In Example 1, a slide bar 50 showing the storage range having a start time phase 50a and an end time phase 50b as both ends, an frame of interest marker 52 showing the time phase (frame of interest) of the image of interest in the storage range (on the bar 50), and a display image frame marker 54 showing the frame of the image currently displayed in the playback of dynamic images are used as the image of interest explicit information. In the example of FIGS. 6A, 6B, and 6C, the frame of interest is assumed to be set as the sixtieth frame of the whole storage range (150 frames).

Before the playback of dynamic images, the display image frame marker 54 is positioned in the start time phase 50a. When the playback of dynamic images starts, the display image frame marker 54 slides on the slide bar 50 as shown in FIG. 6A following the frame No. of the displayed image. The operator can intuitively grasp in what seconds the image of interest will be displayed by, as shown in FIG. 6B, predicting in what time the moving display image frame marker 54 and the frame of interest marker 52 in a predetermined position will overlap. It is preferable to separately display information explicitly indicating the image of interest instantaneously matching the timing when the display image frame marker 54 and the frame of interest marker 52 overlap. After the image of interest is displayed, images corresponding to remaining frames are displayed as dynamic images and when the last frame is displayed, the display image frame marker 54 is positioned in the end time phase 50b (right end) of the slide bar 50.

A plurality of frames of interest in the storage range may be set. In such a case, the frame of interest marker 52 corresponding to each frame of interest will be displayed in the position corresponding to the slide bar 50.

Example 2

FIGS. 7A and 7B are diagrams of screens illustrating the playback of dynamic images using image of interest explicit information according to Example 2. In Example 2, a slide bar 60 provided in the vertical direction on one end or both ends (both ends in the example of FIGS. 7A and 7B) of the screen and showing the storage range (the playback range or playback time), an frame of interest marker 62 showing the time phase (frame of interest) of the image of interest in the storage range (on the bar 60), and a display image frame marker 64 showing the frame of the image currently displayed in the playback of dynamic images are used as the image of interest explicit information. In the example of FIGS. 7A and 7B, the frame of interest marker 62 and the display image frame marker 64 are illustrated as straight lines in the horizontal direction extending to both ends of the screen. However, the present example is not limited to such an example and may be, for example, line segments in the horizontal direction of the screen. It is preferable to display the frame of interest marker 62 always in the center of the image and to change the frame of interest marker 62 and the display image frame marker 64 in color and transparency. The slide bar 60 can also be made to hide by settings.

Before the playback of dynamic images, the display image frame marker 64 is positioned at the upper end of the slide bar 60. When the playback of dynamic images starts, the display image frame marker 64 is translated downward from above along the slide bar 60 (along a direction indicated by an arrow 68 in FIG. 7A). The operator can intuitively grasp in what seconds the image of interest will be displayed by, as shown in FIG. 7B, predicting in what time the moving display image frame marker 64 and the frame of interest marker 62 positioned in the center of the screen will overlap. It is preferable, like in Example 1, to separately display information explicitly indicating the image of interest instantaneously matching the timing when the display image frame marker 64 and the frame of interest marker 62 overlap. After the image of interest is displayed, images corresponding to remaining frames are displayed as dynamic images and when the last frame is displayed, the display image frame marker 64 is positioned at the lower end of the slide bar 60.

A plurality of frames of interest in the storage range may be set. The frame of interest marker 62 corresponding to each frame of interest will be displayed in the position corresponding to the slide bar 60.

Also, in the above example, when the playback of dynamic images is completed, the display image frame marker 64 is positioned again at the upper end of the slide bar 60 and the playback of dynamic images starts from the image of the frame corresponding to the position of the display image frame marker 64. The above example can be modified. For example, when the playback of dynamic images is completed, the display image frame maker 64 is positioned at the position of the frame of interest and the playback of dynamic images may starts from this. According to this configuration, the operator can playback the frame of interest repeatedly and speedy. Moreover, the operator can confirm the frame of interest, recognize the contents of the frame of interest and playback the dynamic images. As a result, the operator can observe a moving site conveniently.

Example 3

Figure 8:
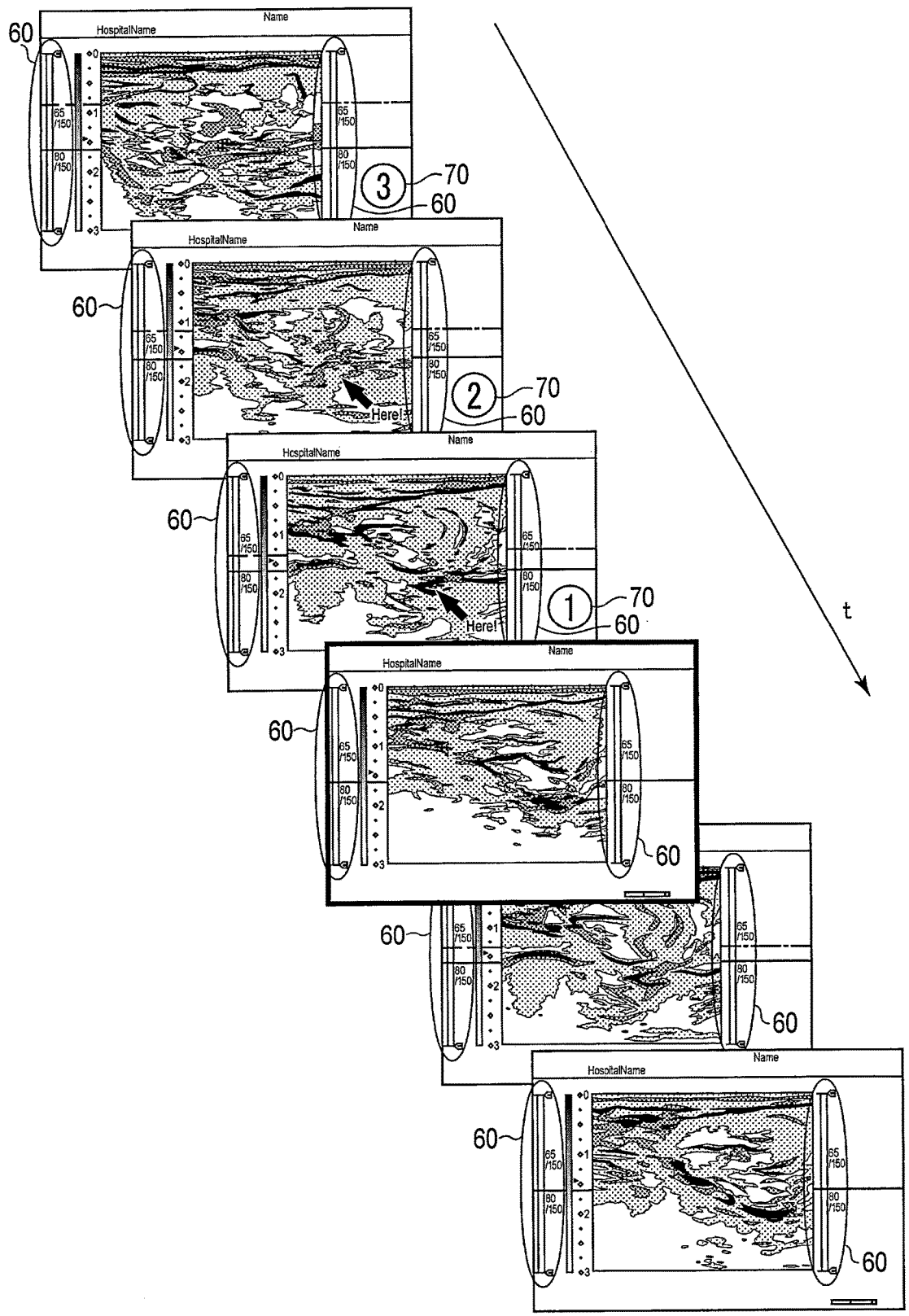
FIG. 8 is a diagram showing an example (countdown information) of the image of interest explicit information generated or displayed in playback processing of dynamic image data according to the present embodiment.

FIG. 8 is a diagram illustrating the playback of dynamic images using image of interest explicit information according to Example 3. In Example 3, a countdown marker 70 is displayed based on the remaining time before the image of interest is displayed as the image of interest explicit information when the display of the image of interest approaches during playback of dynamic images. In the example of FIG. 8, the countdown marker 70 is displayed three seconds before the display of the image of interest and after the countdown display of "(3), (2), (1)", the image of interest is displayed by being highlighted. Accordingly, the operator can intuitively grasp that, for example, "in three seconds, the image of interest will be displayed".

Incidentally, the image of interest explicit information shown in Examples 1 to 3 can arbitrarily be combined. By combining, for example, Example 1 and Example 3 or Example 2 and Example 3, the attention of the operator can further be drawn by causing the countdown marker to appear immediately before the timing when the display image frame marker and the frame of interest marker overlap.

In addition, the image of interest explicit information shown in Examples 1 to 3 can be modified in various ways. For example, Example 3 is configured such that the countdown marker 70 disappears from the screen in the timing of the completion of countdown and the image of interest is highlighted. However, Example 3 is not limited to such an example and in the timing of the completion of countdown, for example, a marker explicitly indicating the image of interest may be caused to appear. Also, in Example 1 or Example 2, when the playback of dynamic images is completed, the display image frame marker may return to the position of the frame of interest marker, instead of returning to the position of the start time phase of the slide bar. According to such a configuration, the image of interest can be played back quickly and easily.

The image of interest may simultaneously be displayed together with dynamic images being played back. In this case, the display size of each image is not specifically limited and, for example, both images may dually be displayed in the same size or the still image may be made smaller in size and superimposed on dynamic images.

According to the dynamic image data playback control function described above, when dynamic image data extending over a predetermined period is played back, the relationship between the predetermined time phase in the predetermined period and the time phase in the predetermined period of the image currently displayed can explicitly be shown simultaneously with dynamic images. Therefore, the operator can intuitively predict the timing when the image of interest valuable for image diagnosis is displayed. As a result, the image of interest can be observed efficiently and also a situation in which necessary information is missed can be avoided.

Example 4

Dynamic image data storage control processing according to Example 4 adjusts the dynamic image storage range or the position (time phase) of the frame of interest set once by using the predetermined GUI when dynamic image data and image of interest identification information are stored.

That is, in the dynamic image data storage control processing according to Example 4, the GUI (for example, the GUI shown in FIG. 3) meeting storage conditions set in advance is displayed in the monitor 14. The operator makes final adjustments of the storage range, the position of the frame of interest and the like for the GUI displayed in the monitor 14. For example, a case in which, as shown in FIG. 3, presets in which the storage range includes a plurality of images (frames) corresponding to 2.0 s and the frame of interest is a frame at 1.4 s point in time of the storage range are changed to the storage range of 3.0 in which the frame of interest is a frame at 2.0 s point in time of the storage range is assumed. The operator can change the storage range and the frame of interest by changing the boundary of the storage range of the displayed GUI and the position of the frame of interest to corresponding positions. By pressing the "Confirm storage" button after the change, image of interest identification information corresponding to storage conditions after the change is generated and stored together with dynamic image data corresponding to the storage range.

Second Embodiment

Next, dynamic image data playback control processing included in an ultrasonic diagnosis apparatus according to the second embodiment will be described. The dynamic image data playback control processing according to the present embodiment realizes observations of more suitable frames of interest by controlling the playback speed in predetermined timing.

A storage/playback control unit 27 controls the dynamic image playback such that when the playback timing of the frame of interest approaches, the playback speed (frames/sec) is slowed down and at least a predetermined number of frames before the frame of interest are played back slowly. For example, regarding dynamic images whose playback speed is set to 30 frames/sec for playback, the storage/playback control unit 27 slows down the playback speed to 10 frames/sec in the timing when the frame a predetermined period before by going back from the frame of interest is reached to play back dynamic images slowly till at least the frame of interest.

The timing or the period of the slow playback can be set by inputting a predetermined number of frames or a predetermined period relative to the frame of interest from an input apparatus 10 or selecting a preset value. Such adjustments of the playback speed are useful when a moving site is observed (when, for example, details of motion of a heart valve are observed).

Third Embodiment

Next, dynamic image data playback control processing included in an ultrasonic diagnosis apparatus according to the third embodiment will be described. The dynamic image data playback control processing according to the present embodiment realizes suitable simultaneous observations of the frames of interest of a plurality of kinds of dynamic images by synchronously playing back the plurality of kinds of dynamic images in a predetermined mode.

In the description that follows, a case when two kinds of dynamic images in a predetermined period in each of which one frame of interest is set are played back side by side is taken as an example. However, the present embodiment is not limited to such an example and the dynamic image data playback control processing according to the present embodiment can also be applied when three kinds or dynamic images or more are played back side by side.

When the synchronous display mode is selected and a plurality of kinds of dynamic images is read, a storage/playback control unit 27 reads supplementary information corresponding to each kind of dynamic images to acquire or calculate playback parameters. Here, the playback parameters include the total number of frames to be played back, the playback speed or playback time, the time phase of the image of interest (frame of interest), the time interval from the playback time of the first frame to the playback time of the frame of interest, the time interval from the playback time of the frame of interest to the playback time of the first frame, and the core time phase of each frame when images are acquired by ECG synchronization. The storage/playback control unit 27 determines the playback mode of the plurality of kinds of read dynamic images according to calculated playback parameters for each kind of dynamic image data to synchronously play back the plurality of kinds of dynamic images.

In the description that follows, examples of the synchronous playback mode of a plurality of kinds of dynamic images are first described to make the description easier to understand and then the operation of the storage/playback control unit 27 including the determination of the synchronous playback mode will be described.

Synchronous Playback Mode Example 1

Figure 9:
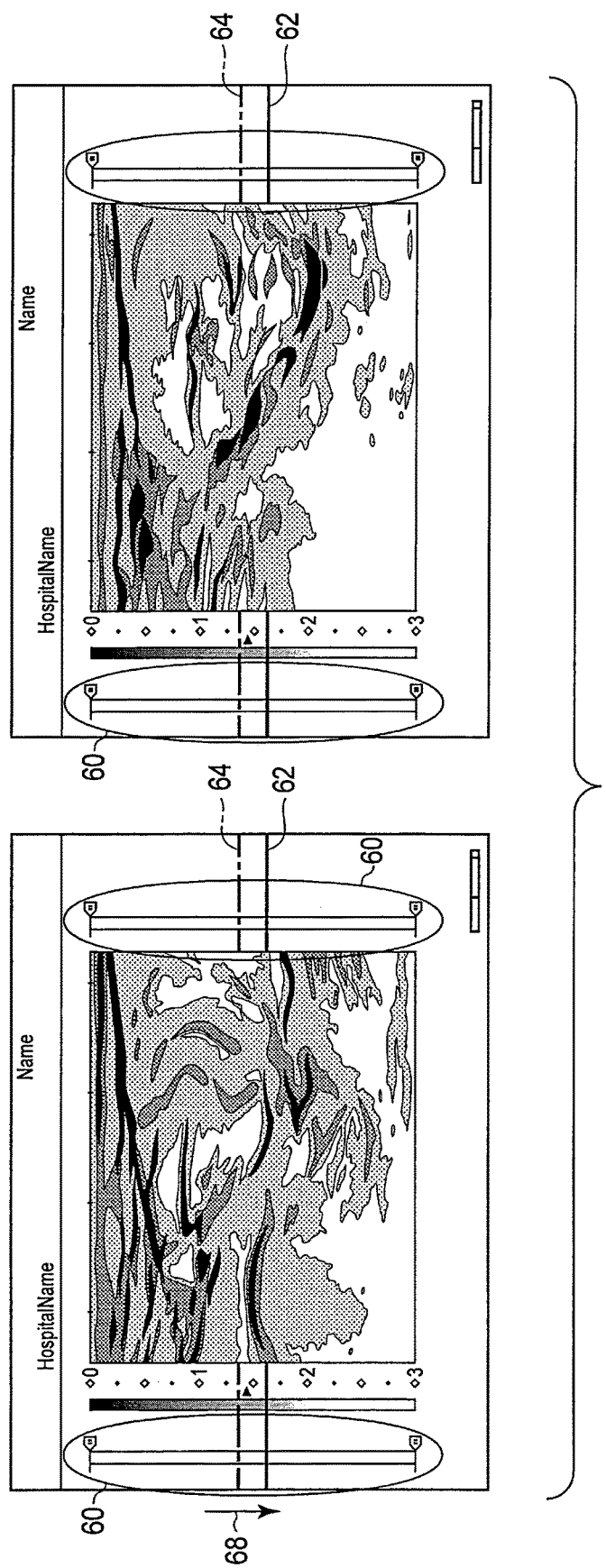
FIG. 9 is a diagram illustrating a synchronous playback mode example 1.

FIGS. 9 and 10 are diagrams illustrating a synchronous playback mode example 1. The example in FIGS. 9 and 10 is a case when the playback times and the time phases of the image of interest (frame of interest) match in playback parameters of two kinds of dynamic images to be played back (therefore, the time intervals from the playback time of the first frame to the playback time of the frame of interest and the time intervals from the playback time of the frame of interest to the playback time of the first frame match). In this case, as shown in FIG. 9 or FIG. 10, the storage/playback control unit 27 matches the lengths and heights of slide bars 60 (slide bars 50) indicating (the playback range or playback time), heights of frame of interest markers 62 (frame of interest markers 52), and moving speeds of display image frame markers 64 (display image frame markers 54) of two kinds of dynamic images for synchronous display.

If two kinds of dynamic images have different total numbers of frames or different playback speeds (for example, dynamic images on the left side in FIG. 9 have the playback speed of 20 frames/sec and dynamic images on the right side in FIG. 9 have the playback speed of 30 frames/sec), update speeds of frames are different on the left and right sides, but dynamic images in which the playback times and the frames of interest are synchronized are played back (this also applies to each of synchronous playback modes described later).

Synchronous Playback Mode Example 2

Figure 11:
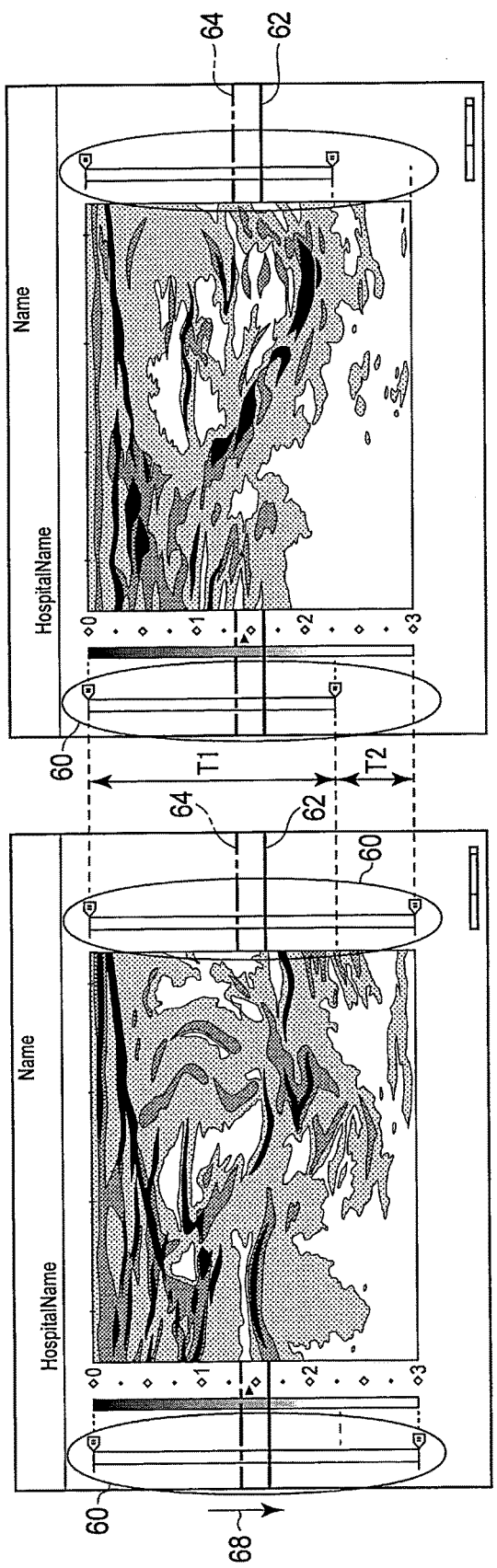
FIG. 11 is a diagram illustrating a synchronous playback mode example 2.

FIG. 11 is a diagram illustrating a synchronous playback mode example 2. The example in FIG. 11 is a case when the playback times are different, but the time intervals from the playback time of the first frame to the playback time of the frame of interest match in playback parameters of two kinds of dynamic images to be played back. In this case, as shown in FIG. 11, the storage/playback control unit 27 matches heights of the upper end (start time) of the slide bars 60 indicating the playback time, heights of the frame of interest markers 62, and moving speeds of the display image frame markers 64 between two kinds of dynamic images to synchronously display left-side dynamic images and right-side dynamic images in a period T1 and to display only left-side dynamic images in a period T2.

Synchronous Playback Mode Example 3

FIG. 12 is a diagram illustrating a synchronous playback mode example 3. The example in FIG. 12 is a case when the playback times and the time intervals from the playback time of the first frame to the playback time of the frame of interest are both different in playback parameters of two kinds of dynamic images to be played back. In this case, as shown in FIG. 12, the storage/playback control unit 27 matches heights of the frame of interest markers 62 and moving speeds of the display image frame markers 64 in the period T2 to synchronously display left-side dynamic images and right-side dynamic images. On the other hand, only left-side dynamic images are played back in the period T1 and only right-side dynamic images are played back in a period T3.

FIG. 13 is a diagram illustrating another synchronous playback mode example 3. In the example in FIG. 13, heights of the frame of interest markers 62 and moving speeds of the display image frame markers 64 of two kinds of dynamic images are matched and left-side dynamic images and right-side dynamic images are played back in the period T2. On the other hand, only right-side dynamic images are played back in the periods T1, T3.

Synchronous Playback Mode Example 4

A case when the playback times and the time intervals from the playback time of the first frame to the playback time of the frame of interest are both different and two kinds of dynamic images are synchronously displayed using the slide bar 50 in the frame reference shown in FIG. 6 is assumed. In this case, for example, as shown in FIG. 14, a mode in which positions of the frame of interest markers 52 are associated for playback can be adopted. In the display mode, on the other hand, if, for example, playback speeds are different, moving speeds of the display image frame markers 54 are different between two kinds of dynamic images, which makes it difficult to grasp temporal correspondences.

In FIG. 14, for example, a case when the slide bar 50 in the upper portion plays back 150 frames in the playback speed of 30 frames/sec and the slide bar 50 in the lower portion plays back 90 frames in the playback speed of 20 frames/sec is assumed. In this case, the display image frame marker 54 in the upper portion moves from the left end to the right end of the slide bar 50 in 5 sec and the display image frame marker 54 in the lower portion moves from the left end to the right end of the slide bar 50 in 4.5 sec. Thus, the display timing of the frame of interest is not synchronized in the playback of two kinds of dynamic images and it is difficult to grasp temporal correspondences.

Thus, in the synchronous playback mode example 4, the playback range of the dynamic images (the number of the frames to be playback) is normalized based on the playback time. In the response to the normalization of the playback range, the moving speed of the display image frame marker 54 is normalized based on the playback time. As a result, the whole of the normalized control of the playback is visualized by the normalized slide bar 50. That is, the length of the slide bar 50 in the upper portion of FIG. 14 does not indicate the number of frames and is defined to correspond to the playback time of 5 sec. According to the definition, the storage/playback control unit 27 corrects (normalizes) the length of the slide bar 50 in the lower portion of FIG. 14 as indicating the playback time of 4.5 sec. Further, the storage/playback control unit 27 synchronously plays back two kinds of dynamic images while displaying, as shown in FIG. 15, the slide bars 50 in which positions of the frame of interest markers 52 and moving speeds of the display image frame markers 54 are associated and normalized.

In the example of FIG. 15, dynamic images in the upper portion and dynamic images in the lower portion are synchronously played back in the period T2. On the other hand, only dynamic images in the lower portion are played back in the period of T1 and only dynamic images in the upper portion are played back in the period of T3.

Synchronous Playback Mode Example 5

In some cases, playback times of two kinds of dynamic images to be played back are doubly or more different in length. In such a case, only dynamic images of a longer playback time are played back in a period after the playback of dynamic images of a shorter playback time is completed and synchronous playback provides almost no advantage. Thus, in the synchronous playback mode example 5, when playback times of two kinds of dynamic images to be played back are doubly or more different in length, dynamic images of a shorter playback time are played back repeatedly (loop playback). Such a mode is useful, for example, for dynamic images of a circulatory organ or two kinds of dynamic images acquired in synchronization with ECG and having different heart rates between both.

(Operation)

Figure 16:
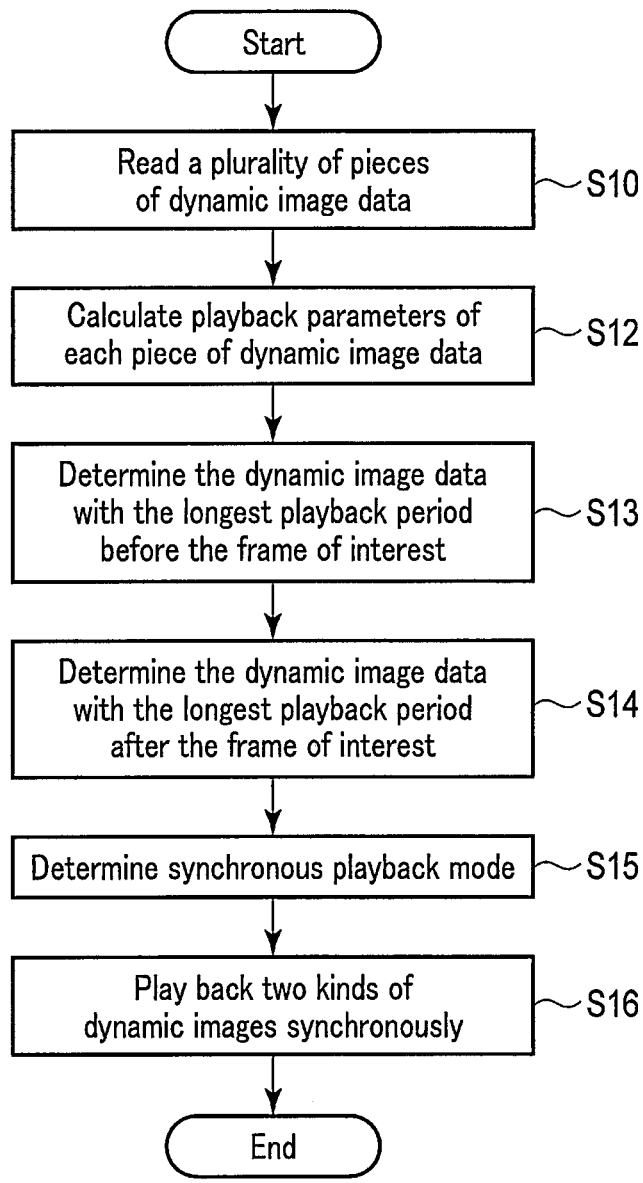
FIG. 16 is a flow chart showing the flow of dynamic image data playback control processing according to the present embodiment.

FIG. 16 is a flow chart showing the flow of the dynamic image data playback control processing according to the present embodiment. As shown in FIG. 16, in response to input from the input apparatus 13, the storage/playback control unit 27 shifts to the synchronous display mode and also reads a plurality of pieces of dynamic image data to be synchronously displayed and supplementary information corresponding to each piece of dynamic image data from a storage unit 32 (Step S10).

Based on the supplementary information, the storage/playback control unit 27 acquires/calculates playback parameters of each piece of dynamic image data (Step S11). The storage/playback control unit 27 also determines, among plurality of pieces of dynamic image data, the dynamic image data with the longest playback period before the frame of interest (that is, the time interval from the playback time of the first frame to the playback time of the frame of interest) and the dynamic image data with the longest playback period after the frame of interest (that is, the time interval from the playback time of the frame of interest to the playback time of the first frame) based on the acquired playback parameters (Steps S12, S13).

Based on playback parameters for each piece of dynamic image data and determination results in Steps S12 and S13, the storage/playback control unit 27 determines which synchronous playback mode to apply (Step S14). For example, when first dynamic image data and second dynamic image data in the same playback period are synchronously played back, if the storage/playback control unit 27 determines that the first dynamic image data is longer than the second dynamic image data in Step S12 and the second dynamic image data is longer than the first dynamic image data in Step S13, the storage/playback control unit 27 determines to apply the synchronous playback mode example 2 shown in FIG. 12.

The storage/playback control unit 27 synchronously plays back two kinds of dynamic images using the synchronous display mode determined in Step S14 (Step S15).

According to the configuration described above, when dynamic images with a registered frame of interest are simultaneously played back side by side, at least the display timings of the frames of interest can automatically be synchronized even if the playback times or playback speeds are different between dynamic images. Therefore, the observer can observe the frames of interest in a plurality of kinds of dynamic images simultaneously without performing a complex display operation. Particularly, this is a useful playback method for prognostic observations of an injury and when a display operation cannot be performed sufficiently.

The present invention is not limited to the above embodiment as it is and can be embodied by modifying structural elements without deviating from the spirit thereof in the working stage. Concrete modifications include, for example, the following:

(1) For example, each function according to the present embodiment can also be realized by installing a program that performs relevant processing on a computer such as a workstation and expanding the program on a memory. In this case, the program capable of causing the computer to perform the relevant techniques can be distributed by storing the program in a recording medium such as a magnetic disk (such as a floppy (registered trademark) disk and a hard disk), an optical disk (CD-ROM, DVD and the like), or a semiconductor memory.

(2) The above embodiment is configured such that image data of frames included in the storage range is cut out from time series image data and stored. However, the above embodiment is not limited to such an example and, for example, mark information identifying a start frame and an end frame may be added to the time series image data to enable the playback or loop-playback by limiting to the range from the start frame to the end frame. According to such a configuration, data having the original time series image data lessened can be generated and the storage area of the apparatus can effectively be used. From the viewpoint of ease-of-use, on the other hand, data on the range from the start frame to the end frame defined by the marker information can separately be stored. In the playback configured as described above, the display using the aforementioned image of interest explicit information can be made by adding marker information identifying the frame of interest in the range from the start frame to the end frame.

(3) The word "processor" used in the above description means, for example, a dedicated or general-purpose processor, circuit (circuitry), processing circuit (circuitry), operation circuit (circuitry), or arithmetic circuit (circuitry), or an application specific integrated circuit (ASIC), or a programmable logic device (for example, a simple programmable logic device (SPLD), a complex programmable logic device (CPLD), or a field programmable gate array (FPGA)). Each component (each processing unit) in the present embodiment is not limited to a single processor and may be realized by a plurality of processors. Further, a plurality of components (a plurality of processing units) may be realized by a single processor.

Also, various inventions can be made by appropriately combining a plurality of structural elements disclosed in the above embodiment. For example, some structural elements may be deleted from all structural elements shown in an embodiment. Further, structural elements from different embodiments may appropriately be combined.

The invention claimed is:

1. A medical image diagnosis apparatus, comprising:
designation circuitry that designates an image corresponding to a predetermined time phase from among a plurality of images in a time series collected by extending over a plurality of time phases;
determination circuitry that determines a starting time and an ending time of a first period based on a predetermined storage ratio before and after the predetermined time phase; and
storage control circuitry that causes a memory to store, among the plurality of images, a plurality of images in the time series corresponding to the first period including a time phase of the designated image and first information explicitly showing the time phase of the designated image in the first period.

2. The medical image diagnosis apparatus according to claim 1, wherein the determination circuitry determines the first period by using the time phase corresponding to the designated image as a reference.

3. The medical image diagnosis apparatus according to claim 1, wherein the determination circuitry determines the first period based on an electrocardiographic waveform.

4. The medical image diagnosis apparatus according to claim 1, wherein the medical image diagnosis apparatus is one of an ultrasonic diagnosis apparatus, an X-ray computerized tomographic apparatus, and a magnetic resonance imaging apparatus.

5. A medical image processing apparatus, comprising:
designation circuitry that designates an image corresponding to a predetermined time phase from among a plurality of images in a time series captured by extending over a plurality of time phases;
determination circuitry that determines a starting time and an ending time of a first period based on a predetermined storage ratio before and after the predetermined time phase; and
storage control circuitry that causes a memory to store, among the plurality of images, a plurality of images in the time series corresponding to the first period including a time phase of the designated image and first information explicitly showing the time phase of the designated image in the first period.

6. The medical image processing apparatus according to claim 5, wherein the determination circuitry determines the first period by using the time phase corresponding to the designated image as a reference.

7. The medical image processing apparatus according to claim 5, wherein the determination circuitry determines the first period based on an electrocardiographic waveform.

8. The medical image processing apparatus according to claim 5, wherein the medical image processing apparatus is one of an ultrasonic diagnosis apparatus, an X-ray computerized tomographic apparatus, and a magnetic resonance imaging apparatus.

* * * * *